United States Patent [19]

Bryant

[11] Patent Number: 4,643,967

[45] Date of Patent: Feb. 17, 1987

[54] ANTIBODY METHOD FOR LOWERING RISK OF SUSCEPTIBILITY TO HLA-ASSOCIATED DISEASES IN FUTURE HUMAN GENERATIONS

[76] Inventor: Bernard J. Bryant, 509 Scripps Dr., Davis, Calif. 95616

[21] Appl. No.: 626,903

[22] Filed: Jul. 2, 1984

Related U.S. Application Data

[63] Continuation of Ser. No. 511,898, Jul. 7, 1983, abandoned.

[51] Int. Cl.$^4$ .............................................. G01N 33/53
[52] U.S. Cl. ........................................ 435/7; 436/543
[58] Field of Search ............................ 435/7; 436/543

[56] References Cited

U.S. PATENT DOCUMENTS 4,191,749 3/1980 Bryant ..................................... 435/2

OTHER PUBLICATIONS

Dausset—Science vol. 213 Sep. 25, 1981 pp. 1469–1474.
A. Svejgaard—Transplantation Proceed, vol. 13 (1981) p. 914.
Anderson et al.—J. of Immunol. vol. 129 (1982) pp. 452–454.
Isojima et al.—Chem. Abst. vol. 97 (1982) pp. 142,832 z.

*Primary Examiner*—Sam Rosen
*Attorney, Agent, or Firm*—Leonard Bloom

[57] ABSTRACT

A method and apparatus for reducing the risk of occurrence in human offspring of diseases in which the susceptibility of the individual is known to be linked to the gene complex encoding the human leukocyte antigens (HLA). Antibody molecules specific for an HLA antigen having a known disease association are used to deplete native semen samples with respect to spermatozoa bearing the targeted HLA antigen on their surface membranes while leaving unaffected, and suitable for fertilization, other spermatozoa in the sample which lack the disease-associated HLA antigen. The specific depletion is effected by cellular killing or inhibition of motility through linkage of the HLA antibody bound by spermatozoa to a cytotoxic molecule such as complement.

30 Claims, 1 Drawing Figure

ANTIBODY METHOD FOR LOWERING RISK OF SUSCEPTIBILITY TO HLA-ASSOCIATED DISEASES IN FUTURE HUMAN GENERATIONS

This application is a continuation of application Ser. No. 511,898, filed July 7, 1983, now abandoned.

BACKGROUND OF THE INVENTION

The instant application relates generally to the immunological techniques applied to native semen, and more specifically to a method for lowering the risk of the susceptibility to certain human diseases related to the human leukocyte antigen which is surface-affixed to human spermatozoa.

A large body of scientific data indicates that the risk of developing many chronic diseases is associated with specific antigens of the human leukocyte antigen (HLA) complex. Since the HLA antigens are surface-affixed to human spermatozoa in specific regions, it is possible with the method revealed hereinafter to expose an HLA antibody to spermatozoa in a semen sample and, after binding of the antibody to the HLA antigen, thereafter separate and eliminate the spermatozoa bearing a specific disease-associated HLA antigen from the remaining population. Spermatozoa lacking the disease-associated HLA antigen can thereinafter be used in artificial insemination to produce human offspring in which the possibility of the occurrence of an HLA associated disease has been greatly reduced. This process may be used when an analysis of the medical history of a prospective father or his family reveals a disease process associated with an HLA antigen expressed by the prospective father.

The prior art of which applicant is aware that may be germane to the patent process is as follows:

U.S. Pat. No. 4,191,749, Bryant;
U.S. Pat. No. 4,265,873, Sheehy et al;
U.S. Pat. No. 4,318,886, Kawahara et al;
Schaller, HOSP.
Dausett NATURE 225:191, 1970
Festenstein, Chapter 2 in *Spermatozoa, Antibodies, and Infertility*, 1978

Of great interest are the discoveries by Dausett and Festenstein which indicate that HLA antigens are expressed on individual sperm in accordance with the chromosome which it receives during meiotic segregation of the chromosome pair encoding HLA genes. Thus, the presence of a certain HLA antigen on the surface of the sperm indicates the presence of a corresponding gene contained in the haploid genetic material within the nucleus of the sperm cell. Therefore, a specific HLA gene produces a correspondingly specific HLA antigen which appears on the outer surface of the spermatozoa allowing binding by a specific antibody to the antigen. The binding and eventual elimination of the undesired sperm can be accomplished by the process revealed in the instant application without negatively affecting the remaining population of sperm in any given semen sample.

The patents to Kawahara et al and Sheehy et al are of general interest in that they reveal methods for typing human leukocyte antigens. Once typed, the antigens can be more specifically identified and an antibody can be produced which is specifically directed to that antigen. However, the aforecited patents and the Schaller article provide only background information which would not appear to impinge on the patentability of applicant's invention.

The remaining citation, being applicant's own patent, reveals a method of isolating sperm cells according to antigens indicative of the sex of an offspring that would result from the fertilization of an egg by a specific sperm. Applicant revealed in his previous patent a method for attaching a male specific antibody to a neutral bead, stacking the beads in a column, and passing a population of spermatozoa therethrough so that male specific spermatozoa were bound to the immunoabsorbent column of beads and female specific spermatozoa were not. After elution of the column the female specific spermatozoa can be retrieved from the medium. Similarly, the male specific spermatozoa may be eluted from the columns by employing the principle of competitive inhibition of cellular binding or other means, after which the male specific spermatozoa are available for artificial insemination.

The technology revealed in the instant application is distinguished from applicant's own prior art in that the instant application is directed towards the prevention of certain chronic diseases of genetically based susceptibility in human offspring, whereas the prior art patent was directed towards the sex selection of mammalian offspring. Furthermore, there are significant differences between the antigens produced by the sex chromosomes and the human leukocyte antigens produced by other chromosomes. There is significant debate in the scientific community as to whether or not the human leukocyte antigens affixed to the surface of spermatozoa are a product of the haploid genetic material contained within the cell itself or a product of the precursor diploid cell. Therefore, it is neither anticipated nor obvious to apply the methods and apparatus revealed in applicant's previous patent to the human leukocyte antigens in order to isolate a specific population of spermatozoa containing undesirable genetic characteristics as is accomplished by applying the methods to be revealed hereinafter.

OBJECTS AND SUMMARY OF THE INVENTION

Accordingly, it is a primary object of the present invention to provide a novel method to greatly reduce the occurrence of HLA-associated diseases in human offsprings by killing or removing prior to artificial insemination of a semen sample those spermatozoa which carry undesirable genetic characteristics.

It is a further object of the present invention to provide individuals having family or personal histories of disease related to a human leukocyte antigen with the ability and peace of mind associated therewith to have children without the fear that any one offspring may have a genetically based heightened susceptibility in later life to such diseases as arthritis, diabetes, schizophrenia, or to other diseases such as myesthenia gravis, systemic lupus erythematosis, and multiple sclerosis, all of which are HLA associated.

It is a still further object of the present invention to provide a novel method to bind HLA specific antibodies to the surface-affixed HLA antigens of individual spermatozoa to provide a means of identifying such antigens on spermatozoa prior to selectively killing or removing spermatozoa bearing such antigens from the rest of the population.

It is yet another object of the present invention to provide a means to prove that a given the surface-affixed human leukocyte antigen is a product of the genetic code contained in the haploid material of the individual sperm cell to which it is affixed and not a result of the chromosome material in the precursor diploid cell.

It is still a further object of the present invention to provide a novel method to separate the undesirable sperm population by linking monospecific HLA antibody to a solid phase ligand such as a bead or magnetic particle which acts to retain only the disease-associated sperm population so that the remainder of the population can be isolated by free migration or elution.

It is a still further object of the present invention to provide a novel method to isolate and incapacitate an undesirable sperm population without any cytotoxic effects to other tissues or sperm by blocking motility or specifically killing HLA antibody-targeted sperm, thereby allowing the conception to occur using natural insemination instead of artificial insemination.

It is a still further object of the present invention to provide a novel method for selectively killing or eliminating spermatozoa bearing a specific disease-associated HLA antigen from other spermatozoa contained in a semen sample that can be manufactured easily and directed toward those in need in the most cost effective manner.

It is yet another object of the present invention to provide the medical and world community with a tool to aid in the family planning of couples with family histories of diseases associated with the human leukocyte antigen.

These and other objects will become manifest when considered in the light of the following detailed description when taken in conjunction with the appended charts and diagrams.

DESCRIPTION OF THE PREFERRED EMBODIMENT

Figure 1:
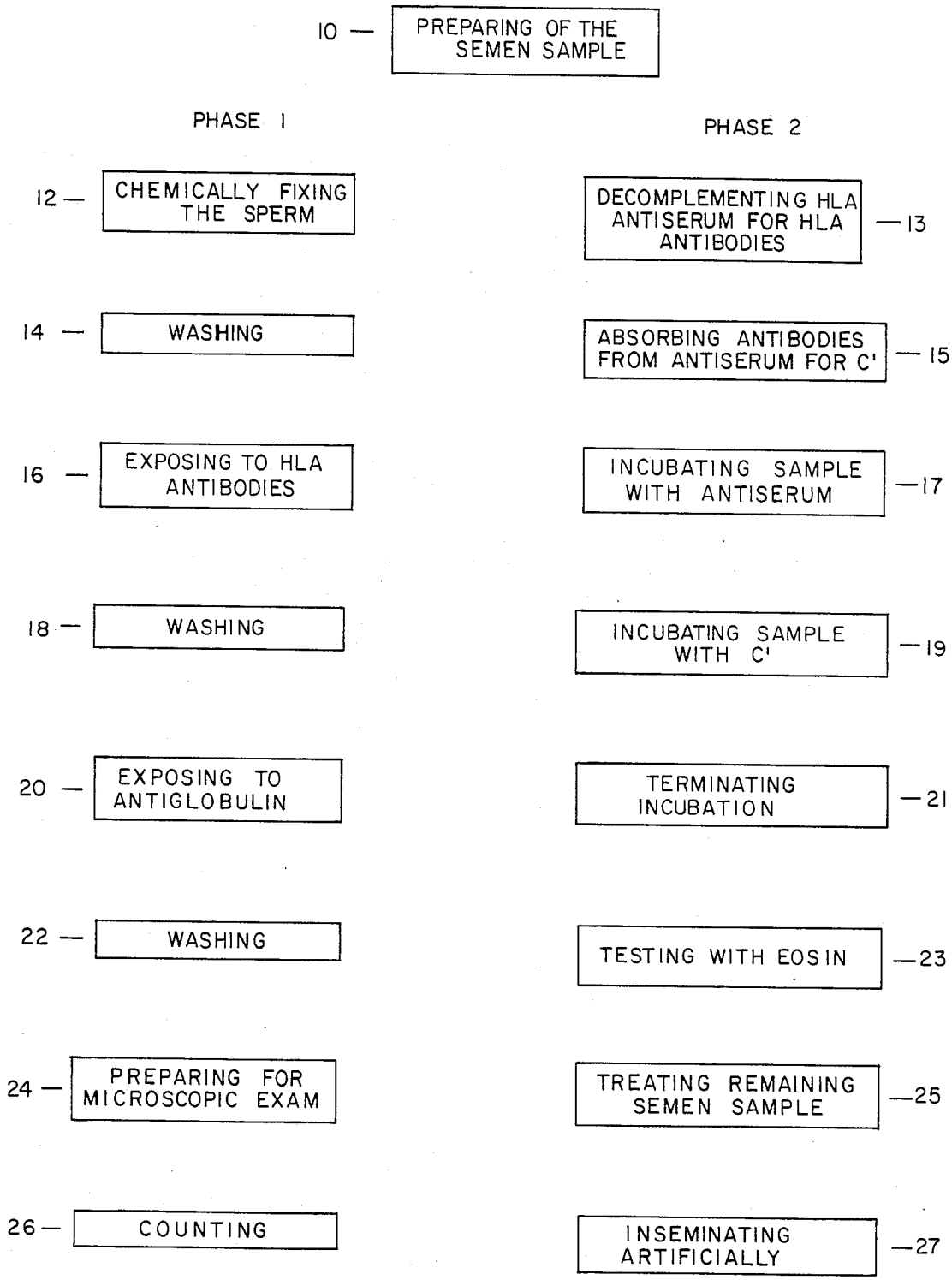
FIG. 1 represents a flowchart of the steps comprising the methods of the instant invention.

Since the present invention is directed towards reducing offspring susceptibility to certain diseases related to specific human leukocyte antigens, it is necessary prior to artificial insemination of the mother to treat the sperm population of a prospective father to selectively kill or reduce the numbers of those sperm which carry the specific HLA antigen targeted for removal.

As is known to one skilled in the art of genetics, the precursor cell to the spermatozoa divides during the process of meiosis during which the members of each pair of chromosomes are segregated to different cells, so that each mature spermatozoan contains only one-half (the haploid number) of the numbers of chromosomes contained in the precursor diploid cell. Whether the surface-affixed HLA antigens on the sperm cell are a product of the chromosome material of the precursor cell or the expression of the haploid chromosome material in the mature sperm cell is a matter of scientific debate; therefore it is necessary to insure that the HLA antigens on the spermatozoa in the particular semen sample are a matter of haploid expression by subjecting a portion of the sample to a fluorescent antibody (FA) study. The FA study represents phase one (see the attached drawing) of the method revealed in the instant application. The FA study insures that the surface-affixed HLA are indicative of the related genetic material within that specific spermatozoa.

After verifying haploid expression, the remainder of the semen sample is treated according to phase two (see the attached drawing) which greatly reduces the population of spermatozoa having the undesired HLA factor. Phase one and phase two of the method according to the instant application will be described in great detail hereinbelow, however it is first necessary to prepare the semen sample according to the following procedure (flowchart reference numeral 10). Preparation of the sperm is performed in 12×75 mm tubes at 20° C. unless otherwise noted. The media used herein refer to buffered balanced salt solutions which may contain an energy source (e.g., fructose or glucose) and which have an osmotic pressure of 270 to 370 milliosmoles (e.g., Medium J) (see Table 1). Such media may be supplemented with either mammalian serum albumin alone (e.g., Medium K) or in combination with Ca and Mg ions (e.g., Medium KS) (see Table 1). Furthermore, the media delineated in Table 1 are examples and examples only of some of a variety of buffered balanced salt solutions which may be employed in conjunction with applicant's disclosure and applicant should not be limited to those solutions delineated in Table 1. The centrifugations employ a horizontal head rotor. The semen sample is dispursed into ten volumes of medium K and centrifuged at 500 rpm for ten minutes to remove cellular aggregates and debris. The supernatant is decanted into a new tube and centrifuged at a speed sufficient to pelletize individual spermatozoa at the bottom of the tube within a period of a few minutes (e.g., the 2,200 rpm/6 minute combination recommended routinely below). The pelleted sperms are resuspended in medium J or KS, counted in a hemacytometer, and adjusted by addition of medium to a working concentration (e.g., 25 million sperms per millilter).

Once the semen sample has been prepared according to the above procedure it is ready to be treated according to the methods of the instant application. However, it should be understood that the present invention is not strictly limited to the steps disclosed hereinafter, since one skilled in the art of immunology may vary the steps and methods according to well known prior art techniques without the exercise of invention.

Phase one involves the steps of the FA (fluorescent antibody) study which is a method known to the prior art as indirect immunofluorescence technique. Using this prior art technique, cells are first washed in an artificial medium, exposed to antiserum containing an antibody capable of binding to a specific cellular antigen, again washed to remove excess unbound antibody, then exposed to a flourescent second antibody capbable of binding to the first antibody, again washed to remove unbound fluorescent antibody and finally prepared on microslides for microfluroescence microscopy. The fluorescent (FA) staining that is observed reveals not only which cells in the preparation express the antigen, but also the distribution or site of fixation of the antigen on individual cells. It should be noted that microfluorescence microscopy is only one of a number of immunological techniques known to one skilled in the art of immunology which could be applied to accomplish the phase one study delineated hereinabove and that applicant also contemplates using such techniques as immunoelectron microscopy and immunoenzyme microscopy to accomplish the phase one study.

Applicant's experience with this prior art technique revealed that it was first necessary before application of the antisera to chemically fix the cells under conditions which would immobilize the sperm surface membrane but not denature the surface-affixed HLA antigens. The fixation prevents the HLA/antibody complex formed on the surface of the spermatozoa from being rapidly internalized and degraded as it is in live spermatozoa. The complex remains on the surface where it can bind the fluorescent second antibody. Thus phase one of the method according to the instant application, i.e., the FA staining technique, is used to insure that the HLA complex has not been internalized or otherwise lost from the cell and that the sample is indicative of the expected haploid expression which is verified if the anticipated fifty percent of the spermatozoa are observed and counted carrying the fluorescent tag. The methods and steps of phase one are delineated in greater specificity in the text hereinbelow which follows the attached flowchart.

As indicated by reference numeral 12, an aliquot of the sperm suspension in medium J (see Table 1) is added for fixation to ten or more volumes of cold one percent glutaraldehyde in medium J, fixed at 4° C. for fifteen minutes, centifuged out at 2,200 rpm for six minutes and resuspended in 5 ml of medium K (see Table 1). This insures the chemical fixing of the sperm cells.

Referring now to reference numeral 14, the fixed sperms are washed by pelleting a second time by centrifugation at 2,200 rpm for six minutes, then the supernatant is decanted, the remaining material then being resuspended in 100 μl medium K (see Table 1), counted by hemacytometer and adjusted by addition of medium K to a concentration of 10 million sperms per ml.

The fixed sperm suspension is now ready for exposure to the HLA antibody. This is accomplished by combining 50 μl of washed, fixed sperm suspension containing 500,000 sperms and 10 μl of commercial HLA antiserum such as that obtained from Accugenics Corp., Costa Mesa, Calif. The combination of the fixed sperm suspension and the HLA antiserum is incubated for fifteen minutes with gentle rotation of the tubes on a mechanical rocker (Tekpro Rotator). The incubation is terminated by adding 5 ml of medium K, centrifuging at 2,200 rpm for six minutes and resuspending the cells in 5 ml of medium K.

Referring now to reference numeral 18, the suspension is again washed by centrifuging at 2,200 rpm for six minutes, decanting and resusending the pellet in 50 μl medium K.

The resuspension is now prepared for exposure to the antiglobulin as indicated by reference numeral 20. 100 μl of FA (fluorescein-tagged goat antihuman globulin obtained from Accurate Chemical and Scientific Corp., Westbury, N.Y.) is diluted 1:5 in medium K and added to the 50 μl of resuspended pellet. This mixture is incubated fifteen minutes, then terminated by adding 5 ml medium K, centrifuging at 2,200 rpm for six minutes, decanting, and resuspending in medium K as indicated above. This resuspension is again washed, as indicated by reference numeral 22, using the exact same procedures delineated hereinabove.

The resuspension is then ready for microscopic observation, reference numeral 24, which is accomplished by resuspending the cells in 50 μl of medium K and preparing wet mount slides for epifluorescence microscopic examination at 250× magnification. One hundred or more sperms are examined on each slide for the presence or absence of specific fluorescence. The results are tabulated by counting, as indicated by reference numeral 26.

Applicant has applied the steps and procedures delineated above in phase one upon many occasions and experience reveals specific FA staining in approximately one-half of all sperms after exposure to antisera to either HLA antigens A1 or A3 but not A2 or A9, see Table 2. The HLA antigens expressed on an individual mature sperm theoretically can reflect either its own genetic composition (haploid gene expression) or that of its diploid precursor cell. Haploid expression in the present instance predicts that the sperm population as a whole will be divided equally into subpopulations of A1 positive and A3 positive cells. This is verified by the results of FA staining using A1 or A3 antisera as shown in Table 2. This interpretation is further verified by the additive effect (nearly 100% FA staining of sperms) observed when A1 and A3 antisera were used together, see Table 2. The few FA positive sperms observed after exposure to A2 or A9 antisera probably express the known presence of extraneous HLA antibodies in the commercial tissue typing antisera used. Thus the results of the methods and steps employed in phase one of the instant invention verify haploid expression, and tissue types the semen donor as positive for HLA A-locus antigens A1 and A3. After phase one has been completed and the semen sample has been verified for haploid expression and particular tissue typing, then the remainder of the sample can be treated before artificial insemination according to the steps of phase two delineated hereinbelow.

The instant invention in all of its embodiments uses specific HLA antibodies to eliminate sperm of one of the two haplotypes without affecting sperm of the other haplotype.

As is well known to one skilled in the art of immunology, human serum contains a cytotoxic molecular complex known as complement (C') and a wide range of antibodies which are specific to certain antigens and will attach thereto. Once attached the antibody molecular structure is physically modified in such a manner that complement recognizes the change and attaches to the modified antibody forming a complex which results in the death of the cell to which it is attached due to lesions in the cell membrane. Thus the complement attaches only to bound antibody and not unbound antibody.

The first two steps of phase two described hereinbelow are directed towards obtaining a supply of complement without antisperm antibodies and HLA antiserum without complement. The antibodies obtained will be essentially monospecific to a particular HLA locus, the type of monospecificity being coordinated with the tissue typing of the individual involved.

Referring now to the flowchart phase two, the initial step, reference numeral 13, involves decomplementing commercially obtained HLA antisera. This is accomplished by heating the antisera at 56° for thirty minutes. The HLA antiserum can be a human serum such as that commercially available from Accugenics Corp., Costa Mesa, Calif. The heating of the serum destroys the immunological function of the complement, but does not destroy the ability of the antibodies to bind to the specific antigens to which they are affiliated. Thus the step referenced 13 provides the essential antibodies, largely monospecific, for a certain HLA antigen.

Next it is necessary to obtain complement free of antibodies, which can bind to sperm antigens, as indicated by reference numeral 15 in the flowchart. This is accomplished by absorbing the antisperm antibody from the complement by serially exposing the complement to fresh sperm populations which attach and bind the antibodies contained in the complement. The suspension thereafter is centrifuged, the complement being decanted and the process being repeated five times until substantially all the antisperm antibody has been removed from the complement. In greater specificity, a semen sample, not necessarily from the same donor, is prepared by washing in medium K as previously described hereinabove. The sperm suspension is added to the complement at a ratio of 3 ml complement per 25 million sperm per absorption. The combination of complement and sperm is gently agitated for a period of sixty minutes by a tube rocker than the sperm is removed by means of centrifugation at 2,200 rpm for six minutes. The complement is then decanted and the process is repeated a total of five times which insures a substantial removal of the antibodies contained therein. Thus after step 15 a supply of complement devoid of antisperm antibodies is provided.

Referring now to flowchart reference numeral 17, a portion of the semen sample to be treated is diluted and suspended in medium KS (see Table 1) at a concentration of 750,000 sperms to 30 $\mu l$ of solution. To this sperm suspension is added 20 $\mu l$ of decomplemented HLA antiserum which was the product of step 13. This mixture of sperm and antiserum is incubated for twenty minutes with gentle agitation on a tube rocker. Applicant's experience through numerous experiments has revealed that an incubation time for step 17 of twenty minutes is an exceedingly critical factor in the ultimate success of the method of the instant invention. A shorter time period does not provide enough of an interval during which the sample population can be fully exposed to the antibodies contained in the antiserum and complete binding of the antibodies to each and every individual in the population does not occur. A time period greater than twenty minutes gives each individual sperm cell in the population the opportunity to internalize the antigen antibody complex across the cell membrane and degrade or dissolve the same into the cellular cytoplasm. Either of these two contingencies would negatively affect the desired results.

It should be noted that alternately and as a control 30 $\mu l$ of medium KS may be substituted for the decomplemented HLA antiserum to establish a control for comparison sake (see Table 2).

It should be noted further that during the incubating step 17 the antibodies in the antiserum are monospecific in relation to the targeted HLA locus, therefore approximately half the sample population would be, for example, A1 positive and the other half of the population would be A1 negative. Thus if an antiserum with monospecificity for A1 antigen were introduced into the sample then half of the population would bind with the antibody introduced, the other half remaining free of antibody binding at that locus. The Table 2 appended hereinafter is an example and an example only of the results when testing an individual who was previously HLA-typed as A1 positive and A3 positive; the additional data provided in Table 2 represents a control and the few FA positive sperms observed after exposure to A2 or A9 antisera probably express the known presence of extraneous HLA antibodies in the commercial tissue typing antisera used.

Referring now to step 19 in the appended flowchart, after the incubation of the sample with the monospecific HLA antiserum for precisely twenty minutes, then 100 $\mu l$ of the five times absorbed complement C' is added to the sample antibody mixture and gentle agitation is continued for another sixty minutes. Then the incubation is terminated in step 21 by adding 2 ml of medium K. The resultant mixture is now ready for an eosin test as performed in step 23 of phase two.

The eosin test will reveal the percentage of sperms killed by C' complement fixation and is performed by combining six drops of diluted incubated sperm suspension with one drop of one percent eosin Y (Sigma Chemical Company, Saint Louis, Mo.) in medium J, then waiting five minutes, then fixing the staining reaction by adding eight drops of one percent glutaraldehyde in medium J. Finally, wet mount microslides are prepared and 100 or more sperms are counted on each slide at a magnification of 250× under phase contrast optics for the presence or absence of the eosin stain. Since the two chromosomes encoding the HLA genes are segregated into separate cells during meiosis, mature sperms comprise two equally numerous subpopulations having different HLA genes. The HLA antigens expressed on an individual mature sperm theoretically can reflect either its own genetic composition (haploid gene expression) or that of its diploid precursor cell. Haploid expression in the present instance predicts that the sperm population as a whole will be divided equally into subpopulations of A1 positive and A3 positive cells. This prediction is verified by the results of the eosin staining test as shown in the data contained in Table 2. Complement fixation as read by the eosin staining effectively eliminated the bulk of the targeted sperms. Of the forty-six percent of sperms dead after exposure to A1 antiserum and complement C' about seven percent where dead A3 positive cells (half of the medium control value) indicating that thirty-nine percent were dead A1 positive cells. Thus among each 100 sperms, there remained alive after A1 antiserum and complement C' treatment about eleven A1 and forty-three A3 positive sperms. The probability of A1 antigen expression in offspring issuing from artificially inseminating an A1 negative mother with this sperm population would therefore approximate 11/11+43 or twenty percent. This represents a significant difference between the normal predication which would be fifty percent. Thus parents having a medical history of HLA-associated disease on the prospective paternal side can significantly reduce the likelihood of occurrence of such disease in their offspring by applying the methods and techniques of the instant application.

Referring now to step 25, the remainder of the semen sample obtained from the prospective father is treated using the steps 17, 19, and 21 and a large enough sample is obtained for use in the final step 27 which employs the well known techniques of inseminating artificially.

It should be noted that the physical condition of any reactant (e.g., its temperature, dilution or concentration) or its time of reaction as described in the various steps hereinabove can be varied unless stated otherwise according to well known principles of immunology or cell biology without departing from the spirit of the invention.

It should be further noted that various well known immunological and cell biological techniques are contemplated as possible alternatives to the various steps described hereinabove, which may all be included or not depending on the necessity of the situation without departing from the spirit of the invention. For example, it will be obvious to one skilled in the art of immunology that cytotoxic substances alternative to the complement used herein, such as ricin or glucose oxidase, can be linked to the HLA antibody molecules to selectively kill or inhibit the motility of HLA antibody-targeted spermatozoa. It will likewise be further obvious to one skilled in the art of immunology that the specific depletion of spermatozoa according to HLA type achieved herein can be alternatively performed by retaining the HLA antibody-targeted spermatozoa on the surface of neutral beads or magnetic particles which have been coated with an antiglobulin or other substance such as protein A capable of binding the HLA antibody molecules bound by the cell.

TABLE 1

| MEDIUM J: | FORMULATION: grams/liter | |
|---|---|---|
| NaCl | 6.238 | |
| KCl | 0.401 | |
| Na$_2$HPO$_4$ | 2.398 | |
| KH$_2$PO$_4$ | 0.563 | |
| Na pyruvate | 0.032 | |
| Na lactate | 2.720 | |
| fructose | 2.000 | pH'd to 7.30 using NaOH |

MEDIUM K: Prepared by adding 1 g globulin-free bovine serum albumin (Sigma Chemical Company, St. Louis, Missouri) to 1 liter of MEDIUM J, pH'd to 7.30
MEDIUM KS: Prepared by supplementing 99.5 ml of MEDIUM K with 0.5 ml of solution containing 25.0 g CaCl$_2$.2H$_2$O and 24.4 g MgCl$_2$.6H$_2$O per liter.

TABLE 2

| HLA Antiserum Pretreatment | Percentage of Sperms | |
|---|---|---|
| | FA Positive | Eosin Postive* |
| A1 | 52 | 46 |
| A2 | 5 | 11 |
| A3 | 54 | 42 |
| A9 | 6 | 10 |
| A1 & A3 | 97 | 89 |
| Medium Control | 0 | 14 |

Mean percentages derived from experiments on sperms from an individual previously typed as positive for HLA-A locus antigens A1 and A3.
*In C' fixation system.

What is claimed is:

1. A method for treating human sperm in order to reduce the probability of human offspring conceived therefrom contracting certain diseases which have genetically transmitted susceptibilities, comprising the steps of:
   (a) decomplementing a sample of HLA antiserum to obtain a specific HLA antibody without complement;
   (b) absorbing a sample of HLA antiserum to obtain complement without any of the specific HLA antibody;
   (c) incubating a portion of sperm sample with the specific HLA antibody obtained from step (a);
   (d) fixing the sperm sample with complement without any of the specific HLA antibody obtained from step (b);
   (e) terminating incubation;
   (f) testing to determine the effectiveness of the specific antibody binding and specific complement fixation; and
   (g) treating the remainder of the sperm sample according to steps (a), (b), (c), (d), and (e);

whereby a targeted population of spermatozoa having a specific HLA antigen expression is killed or eliminated from the sperm sample of a prospective father so that the remainder of the sample is left intact to be used in artificially inseminating a prospective mother thereby reducing likelihood of any offspring conceived therefrom of contracting diseases with genetically transferred susceptibilities associated with the specific target HLA antigen.

2. The method of claim 1, wherein the step of decomplementing further includes:
   choosing at least one antiserum with monospecific HLA antibody contained therein for the HLA locus chosen in accordance with the results of known tissue typing techniques performed on a donor of the human sperm sample, and heating the antiserum within a range of from about 50° C. to about 60° C. for a period of from about 25 to about 35 minutes, whereby complement contained within the antiserum is denatured and rendered inoperable, thus providing a source of a desired monospecific HLA antibody.

3. The method of claim 2, wherein the step of absorbing further includes:
   preparing another source of human sperm to absorb monospecific HLA antibodies from the antiserum by suspending same in a medium to form a suspension;
   adding the suspension to substantially 2 to 4 ml. of the antiserum to form a mixture;
   gently agitating the mixture for substantially from about 50 to about 70 minutes;
   centrifuging the mixture; and
   repeating the preparing, adding, agitating and centrifuging at least five times to serially absorb all the monospecific HLA antibodies from the mixture, leaving only active complement.

4. The method of claim 2, wherein the step of incubating further includes:
   adding substantially from about 15 to about 25 $\mu$l. of the decomplemented antiserum to substantially from 25 to 35 $\mu$l. of the suspension; and
   incubating same at room temperature with gentle agitation for twenty minutes;
   whereby the monospecific antibody in the antiserum binds to those sperms in the suspension expressing the specific targeted HLA antigen.

5. The method of claim 3, wherein the step of fixing further includes:
   adding substantially 100 ul. of the five times absorbed complement obtained in step b to the incubated mixture of the sperm suspension and the decomplemented antiserum to form a new mixture;
   agitating the new mixture for substantially from about 50 to about 70 minutes, whereby the active complement attaches to those sperms having the monospecific antibody bound thereto and kills the sperms with the specific antibody affixed to a specific target HLA antigen; and
   terminating incubation and fixation by adding substantially from 1 to 3 ml. of a salt solution to the new mixture.

6. The method of claim 1, wherein the step of testing further includes:
   staining the new mixture after terminating incubation and fixation by combining several drops of diluted incubated sperm suspension contained in the new mixture with at least one drop of a compatible staining means;

waiting substantially from about 5 to about 10 minutes;

fixing the staining reaction by adding several drops of substantially one percent glutaraldehyde in said first buffered balanced salt solution;

wet mounting the resultant composition on microslides; and counting under microscopic magnification the number of sperms killed in a population of 100, to determine effectiveness of the method in eliminating a targeted sperm population in the semen sample from the donor and further verifying the tissue typing of the donor.

7. The method of claim 1, wherein the step of treating the remainder of the semen sample further includes:

treating the remainder of the semen sample from the donor in volume according to the steps (a), (b), (c), (d), and (e);

incorporating the tested sperms from the semen sample into a fluid medium suitable for use in artificial insemination; and inseminating artificially a human female with the fluid medium containing the treated sperm;

whereby human offspring conceived from the insemination have a greatly reduced probability of contracting certain human diseases known to pass susceptibility thereto genetically by association with the genes responsible for HLA expression.

8. The method of claim 1, wherein the sperm sample is a semen sample prepared for treatment by the steps comprising:

suspending the semen sample in ten volumes of a salt solution;

centrifuging the suspension to remove cellular aggregates and debris providing a supernatent;

decanting the supernatent;

recentrifuging; and resuspending pelleted sperms from the sample in a medium obtained immediately before use by supplementing a buffered balanced salt solution medium with mammalian serum albumin in combination wth Ca and Mg ions.

9. The method of claim 1, wherein the sperm sample is obtained from native semen donated by the donor after the donor has been tissue typed for certain specific HLA loci by known techniques, the specific HLA antibody being a monospecific antibody chosen in accordance with the tissue typing of the donor.

10. The method of claim 1, wherein various HLA loci are selected as the determining factor in separating and eliminating targeted sperm populations in the sperm sample according to disease susceptibilities transmitted by genes associated with selected HLA loci, according to tissue typing of a paternal donor, and according to history of certain diseases in the family of the paternal donor.

11. The method of claim 1, wherein ricin, a cytotoxic substance, is linked to molecules of the specific HLA antibody to selectively eliminate specific HLA antibody-targeted spermatozoa.

12. The method of claim 1, wherein glucose oxidase, a cytotoxic substance, is linked to molecules of the specific HLA antibody to selectively eliminate specific HLA antibody-targeted spermatozoa.

13. The method of claim 1, wherein specific HLA antibody-targeted spermatozoa are retained on the surface of neutral beads coated with fixing means capable of binding a molecule of the specific HLA antibody, the molecule becoming bound to the surface of the targeted spermatozoa.

14. The method of claim 13, wherein said fixing means further comprise antiglobulin and protein A.

15. The method of claim 1, wherein step (f) is effected by testing with eosin.

16. A method for treating sperm in order to reduce the probability of offspring conceived therefrom contracting at least one disease which has a genetically transmitted susceptibility, comprising the steps of:

(a) obtaining at least one specific antibody without complement;

(b) obtaining complement without any of the at least one specific antibody;

(c) incubating a portion of a sperm sample with at least one specific antibody obtained from step (a);

(d) fixing the sperm sample with complement without any of the at least one specific antibody obtained from step (b);

(e) terminating incubation;

(f) testing to determine effectiveness of the specific antibody binding and complement fixation; and (g) treating the remainder of the sperm sample to leave intact substantially only spermatozoa which lack said at least one specific antibody.

17. A method for treating sperm in order to reduce the probability of offspring conceived therefrom contracting at least one disease which has a genetically transmitted susceptibility, comprising the steps of:

(a) obtaining at least one specific antibody without complement;

(b) obtaining complement without any of the specific antibody;

(c) fixing a sperm sample with complement obtained from step (b);

(d) testing to determine effectiveness of antibody binding and complement fixation; and (e) treating the remainder of the sperm to leave intact substantially only spermatozoa which lack said at least one antibody.

18. The method of claim 17, wherein the step of chemically fixing further includes:

suspending an aliquot of the semen sample in a first buffered balanced salt solution medium containing an energy source to provide a suspension, said first salt solution having an osmotic pressure within a range of from about 270 to about 370 milliosmoles;

adding ten or more volumes of a solution within a range of from about 0.25% to about 2% glutaraldehyde in said first salt solution medium to said suspension; and fixing for about 10 to about 20 minutes at a temperature in a range of from about 2° C. to about 6° C.

19. The method of claim 18, wherein said first buffered balanced salt solution medium comprises:

|  | grams/liter |
|---|---|
| NaCl substantially | 6.0 |
| KCl substantially | .4 |
| Na2HPO4 substantially | 2.4 |
| KH2PO4 substantially | .6 |
| Na pyruvate substantially | .1 |
| Na lactate substantially | 2.7 |
| fructose substantially | 2.0, | the salt solution being adjusted to a pH of 7.30 using NaOH.

20. The method of claim 18, wherein the step of washing a second time further includes:
 centrifuging a resultant solution in a tube having a bottom at a sufficient speed to pelletize individual sperms at the bottom of the tube within a period of a few minutes; and
 resuspending the thus pelleted sperms in a volume of said first buffered balanced salt solution supplemented with mammalian serum albumin.

21. The method of claim 18, wherein the step of washing a third time is performed twice to form a preparation containing fixed and exposed sperm and further includes:
 centrifuging a resultant solution in a tube at a sufficient speed to pelletize individual sperms at the bottom of the tube within a period of a few minutes, and
 resuspending the then pelleted sperms in a volume of said first buffered balanced salt solution supplemented with mammalian serum albumin.

22. A method of treating a semen sample for sperms expressing or not expressing as the cases may be specific HLA (human leukocyte antigens), the method comprising:
 (a) chemically fixing sperms in the semen sample;
 (b) washing the semen sample a first time after chemical fixation;
 (c) exposing the semen sample to a specific HLA antibody directed to a specific HLA antigen;
 (d) washing the semen sample a second time;
 (e) exposing the semen sample to fluorescein-tagged antiglobulin;
 (f) washing the semen sample a third time;
 (g) preparing the semen sample for microscopic examination;
 (h) microscopically examining the sperms in the semen sample and calculating the percentage of the counted population of sperms which show specific fluorescence to verify sperms in the semen sample by the applied specific HLA antibody and fluorescent antiglobulin combination as expressing or not expressing a specific HLA antigen in haploid fashion; and
 (i) selecting for use that sample of semen not containing a specific disease-associated HLA antigen.

23. The method of treating a semen sample according to claim 22, wherein the selecting step includes the step of separating those sperms which do not express the specific HLA antigen in haploid fashion from those which do.

24. The method of claim 22, wherein the step of exposing the semen sample containing sperms obtained after the step of washing a first time and constituting a resuspension includes:
 adjusting the resuspension to a concentration of substantially 8 to 12 million sperms per ml. by the addition of a second buffered balanced salt solution supplemented with mammalian serum albumin;
 combining substantially 40 to 50 $\mu$l. of the washed, fixed sperm resuspension with substantially 5 to 10 $\mu$l. of an antiserum monospecific for a chosen HLA locus according to the tissue typing of sperm donor;
 incubating for substantially ten to twenty minutes with gentle agitation; and
 terminating incubation by adding substantially from 5 to 10 ml. of a second buffered balanced salt solution supplemented with mammalian serum albumin.

25. The method of claim 24, wherein said second buffered balanced salt solution further comprises a medium obtained by adding substantially 1 gram of globulin-free bovine to substantially 1 liter of said first buffered balanced salt solution medium and adjusting the pH to substantially 7.3 using NaOH.

26. The method of claim 22, wherein the step of exposing the semen sample to fluorescein-tagged antiglobulin further includes:
 suspending the then washed sperms in substantially 40 to 50 ul, of said second salt solution;
 adding substantially 30 to 100 $\mu$l. of fluorescein-tagged goat antihuman antiglobulin (FA) diluted substantially 1:5 in said second salt solution;
 incubating for ten to twenty minutes; and
 terminating incubation by adding substantially 5 to 10 ml. of said second salt solution.

27. The method of claim 22, wherein the step of preparing the semen sample for microscopic examination further includes:
 resuspending the preparation in substantially 50 $\mu$l. of said second salt solution; and
 preparing wet mount microscopic slides for epifluorescent microscopic examination.

28. The method of claim 22, wherein the step of microscopically examining the sperms in the semen sample further includes:
 observing wet mount slides containing at least 100 sperms from the semen sample thereon;
 counting the sperms manifesting epifluorescence; and
 comparing the count with a predicted amount of fifty percent epifluorescence for a single HLA locus which indicates that the sperms in the semen sample manifest haploid expression for a chosen HLA locus.

29. The method of claim 22, wherein testing is conducted using immunoelectron microscopy.

30. The method of claim 22, wherein testing is conducted using immunoenzyme microscopy.

* * * * *